(12) United States Patent
Eizenman et al.

(10) Patent No.: US 10,085,688 B2
(45) Date of Patent: Oct. 2, 2018

(54) METHOD OF IDENTIFYING AN INDIVIDUAL WITH A DISORDER OR EFFICACY OF A TREATMENT OF A DISORDER

(71) Applicant: El-Mar Inc., Downsview (CA)

(72) Inventors: Moshe Eizenman, Downsview (CA); Oren Eizenman, Downsview (CA)

( * ) Notice: Subject to any disclaimer, the term of this patent is extended or adjusted under 35 U.S.C. 154(b) by 114 days.

(21) Appl. No.: 14/085,291

(22) Filed: Nov. 20, 2013

(65) Prior Publication Data
US 2014/0148728 A1 May 29, 2014

Related U.S. Application Data

(60) Provisional application No. 61/728,260, filed on Nov. 20, 2012.

(51) Int. Cl.
*A61B 5/00* (2006.01)
*A61B 5/11* (2006.01)
*A61B 5/16* (2006.01)

(52) U.S. Cl.
CPC .......... *A61B 5/4848* (2013.01); *A61B 5/1104* (2013.01); *A61B 5/1128* (2013.01); *A61B 5/165* (2013.01); *A61B 5/162* (2013.01); *A61B 5/4088* (2013.01)

(58) Field of Classification Search
CPC ....... A61B 5/11; A61B 5/1103; A61B 5/1104; A61B 5/1128; A61B 5/16; A61B 5/165; A61B 5/168; A61B 5/4848; A61B 3/113; G06F 3/013; H04N 13/0484
See application file for complete search history.

(56) References Cited

U.S. PATENT DOCUMENTS

| | | | | |
|---|---|---|---|---|
| 6,070,098 A | * | 5/2000 | Moore-Ede | A61B 5/7267 600/300 |
| 7,938,785 B2 | * | 5/2011 | Aguilar | A61B 3/112 600/558 |
| 7,959,578 B2 | * | 6/2011 | Lonky | A61B 3/113 600/558 |

(Continued)

OTHER PUBLICATIONS

Hannula, D. et al., "Worth a glance: using eye movements to investigate the cognitive neuroscience of memory", Frontiers in Human Neuroscience, Oct. 2010, vol. 4, Article 166.*

(Continued)

*Primary Examiner* — Rene Towa

(57) ABSTRACT

This invention relates to a method of identifying individuals with neuropsychiatric disorders or to predict and determine the efficacy of treatment of the disorder by acquiring information about visual scanning behavior and fluctuations of visual scanning behavior of individuals comprising presenting to the individual a sequence of visual stimuli, wherein each visual stimulus is comprised of multiple images with specific characteristics, measuring the point-of-gaze of said subject on the visual stimuli and calculating a set of statistical measures that describes the visual scanning behavior of the individual on images or portion of images with the same characteristics; and making a determination of biases in visual scanning behavior of the individual, by comparing the statistical measures of the individual to the statistical measures of controls.

18 Claims, 10 Drawing Sheets

An example of gaze processing sequence.

(56) References Cited

U.S. PATENT DOCUMENTS

| | | | | |
|---|---|---|---|---|
| 2010/0092929 | A1* | 4/2010 | Hallowell | G09B 7/00 434/167 |
| 2011/0109879 | A1* | 5/2011 | Palti-Wasserman | A61B 3/113 351/209 |
| 2013/0090562 | A1* | 4/2013 | Ryan | A61B 3/032 600/473 |

OTHER PUBLICATIONS

Fattahi, P., "Eyetracking Definitions", SensoMotoric Instruments, Apr. 2011, available from http://twiki.cis.rit.edu/twiki/pub/MVRL/SmiTracker/BasicDefinitionofTerms_SMI2.pdf.*

Kimble et al., "Eye Tracking and Visual attention to threating stimuli in veterrans of the Iraq war," J Anxiety Disord. Apr. 2010; 24(3): 293-299.*

Pryor et. al, (1995).The clinical significance of symptom denial among women with anorexia nervosa: Another disposable myth? Eating Disorders: The Journal ofTreatment & Prevent.

Giel, K.H., Friederich, H.C., Teufel, M., Hautzinger, M., Enck, P. and Zipfel, S.,(2011a). Attentional processing of food pictures in Individuals with Anorexia Nervosa—A.

Lang, P.J., Bradley, M.M., Cuthbert, B.N., 1997. International Affective Picture System: Technical Manual and Affective Ratings, NIMH Centre for the Study of Emotion and Atten.

Shafran, R., Lee, M., Cooper, Z., Palmer, R.L., Fairbum, C.G., (2007). Attentional bias in eating disorders. International Journal of Eating Disorders, 40(4):369-80.

Pryor, Tamara L. et al., The clinical significance of symptom denial among women with anorexia nervosa: Another disposable myth?, Eating Disorders: The Journal of Treatment & Prevention, 1995, vol. 3, Issue 4, pp. 293-303.

Bauser, Denise A. Soria et al., Difference between perception of human faces and body shapes: Evidence from the composite illusion, Vision Research, 2011, vol. 51, pp. 195-202.

Dobson, Keith S. et al., Attentional biases in eating disorders: A meta-analytic review of Stroop performance, Clinical Psychology Review, 2004, vol. 23, pp. 1001-1022.

Downing, Paul E. et al., A Cortical Area Selective for Visual Processing of the Human Body, Science, Sep. 28, 2001, vol. 293, No. 5539, pp. 2470-2473.

Eizenman, Moshe et al., A naturalistic visual scanning approach to assess selective attention in major depressive disorder, Psychiatry Research, 2003, vol. 118, pp. 117-128.

Fairburn, Christopher G. et al., Cognitive behaviour therapy for eating disorders: a "transdiagnostic" theory and treatment, 2003, vol. 41, pp. 509-528.

Garner, David M. et al., The Eating Attitudes Test: psychometric features and clinical correlates, 1982, vol. 12, pp. 871-878.

Garner, Matthew et al., Orienting and Maintenance of Gaze to Facial Expressions in Social Anxiety, Journal of Abnormal Psychology, 2006, vol. 115, No. 4, pp. 760-770.

George. H.R. et al., Differences in eye-movement patterns between anorexic and control observers when judging body size and attractiveness, British Journal of Psychology, 2011, vol. 102, pp. 340-354.

Giel, Katrin E. et al., Attentional Processing of Food Pictures in Individuals with Anorexia Nervosa—An Eye-Tracking Study, Biol Psychiatry, 2011, vol. 69, pp. 661-667.

Giel, Katrin Elisabeth et al., Processing of Pictorial Food Stimuli in Patients with Eating Disorders—A Systemic Review, International Journal of Eating Disorders, 2011, vol. 44, Issue 2, pp. 105-117.

Guestrin, Elias Daniel and Eizenman, Moshe, General Theory of Remote Gaze Estimation Using the Pupil Center and Corneal Reflections, IEEE Transactions on Biomedical Engineering, Jun. 2006, vol. 53, No. 6, pp. 1124-1133.

Guestrin, Elias and Eizenman, Moshe, Remote Point-of-Gaze Estimation for Studies of Selective Attention and Mood Disorders, Presented at the 30th Canadian Med. Bio. Conf., 4 pages.

Guestrin, Elias and Eizenman, Moshe, Remote Point-of-Gaze Estimation Requiring a Single-Point Calibration for Applications with Infants, Proceedings of the ETRA, 2008, pp. 267-274.

Hannula, Deborah E. et al., Worth a glance using eye movements to investigate the cognitive neuroscience of memory, Frontiers in Human Neuroscience, Oct. 2010, vol. 4, Article 166, pp. 1-16.

Hermans, Dirk et al., Eye Movement Registration as a Continuous Index of Attention Deployment: Data from a Group of Spider Anxious Students, Cognition and Emotion, 1999, vol. 13, Issue 4, pp. 419-434.

Jansen, Anita et al., Selective visual attention for ugly and beautiful body parts in eating disorders, Behaviour Research and Thearpy, 2005, vol. 43, pp. 183-196.

Johansson, Linda et al., Stroop interference for food- and body-related words: a meta-analysis, Eating Behaviors, 2005, vol. 6, pp. 271-281.

Kellough, Jennifer L. et al., Time course of selective attention in clinically depressed young adults: An eye tracking study, Behaviour Research and Therapy, 2008, vol. 46, pp. 1238-1243.

Lang, P.J. et al., International Affective Picture System (IAPS): Technical Manual and Affective Ratings, NIMH Center for the Study of Emotion and Attention, 1997, 5 pages.

Long, Clive G. et al., Selective Processing of Food and Body Size Words: Application of the Stroop Test with Obese Restrained Eaters, Anorexics, and Normals, International Journal of Eating Disorders, 1994, vol. 15, No. 3, pp. 279-283.

McKhann, Guy et al., Clinical diagnosis of Alzheimer's disease: Report of the NINCDS? ADRDA Work Group under the auspices of Department of Health and Human Services Task Force on Alzheimer's Disease, Neurology, Jul. 1984, vol. 34, pp. 939-944.

Mathews, A. and MacLeod, C., Cognitive Approaches to Emotion and Emotional Disorders, Annu. Rev. Psychol., 1994, vol. 45, pp. 25-50.

Preti, Antonio et al., The epidemiology of eating disorders in six European countries: Results of the ESEMeD-WMH project, Jouranl of Psychiatric Research, 2009, vol. 43, pp. 1125-1132.

Rinck, Mike and Becker, Eni S., Spider Fearful Individuals Attend to Threat, Then Quicky Avoid It: Evidence From Eye Movements, Journal of Abnormal Psychology, 2006, vol. 115, No. 2, pp. 231-238.

Robert, P. et al., Proposed diagnostic criteria for apathy in Alzheimer's disease and other neuropsychiatric disorders, European Pychiatry, 2009, vol. 24, pp. 98-104.

Sears, Christopher R. et al., Attentional biases in dysphoria: An eye-tracking study of the allocation and disengagement of attention, Cognition and Emotion, 2010, vol. 24, No. 8, pp. 1349-1368.

Shafran, Roz et al., Clinical perfectionism: a cognitive-behavioural analysis, Behaviour Research and Therapy, 2002, vol. 40, pp. 773-791.

Shafran, Roz et al., Attentional Bias in Eating Disorders, International Journal of Eating Disorders, 2007, vol. 40, No. 4, pp. 369-380.

Shafran, Roz et al., Effect of Psychological Treatment of Attentional Bias in Eating Disorders, International Journal of Eating Disorders, 2008, vol. 41, No. 4, pp. 346-354.

Smeets, Elke et al., Body Checking Induces an Attentional Bias for Body-Related Cues, International Journal of Eating Disorders, 2011, vol. 44, No. 1, pp. 50-57.

Toh, Wei Lin et al., Current visual scanpath research: a review of investigations into the psychotic, anxiety, and mood disorders, Comprehensive Psychiatry, 2011, vol. 52, pp. 567-579.

Von Wietersheim, Jorn et al., Selective Attention of Patients with Anorexia Nervosa While Looking at Pictures of Their Own Body and the Bodies of Others: An Exploratory Study, Psychosomatic Medicine, 2012, vol. 74, pp. 107-113.

* cited by examiner

Figure 4: An example of gaze processing sequence.

Figure 6: General Block diagram

METHOD OF IDENTIFYING AN INDIVIDUAL WITH A DISORDER OR EFFICACY OF A TREATMENT OF A DISORDER

FIELD OF THE INVENTION

This invention relates to the field of neuropsychiatric testing and in particular to the use of point-of-gaze data to identify an individual with a psychiatric disorder or predicting the efficacy of a treatment of a disorder such as predicting the efficacy of a drug treatment in depression through the statistical analysis and modeling of eye movements and point-of-gaze data.

BACKGROUND TO THE INVENTION

The current standard in assessments of neuropsychiatric disorders includes questionnaires that require verbal interaction with the person (clinician, caregiver etc.) who is conducting the assessment. Examples of commonly used questionnaires for the assessment of neuropsychiatric disorders are the 21-item Hamilton Depression Rating Scale (HAM-D) to assess depression, the 26-item Eating Attitudes Test (EAT-26) to assess eating disorders and the Neuropsychiatric Inventory (NPI) to assess behavioural disturbances in dementia patients. If subjects minimize or amplify the severity of their symptoms or are unable to provide accurate descriptions of their symptoms (e.g., Alzheimer patients) the accuracy of the assessments is compromised. Also, due to the time lag between the start of a therapeutic regime and alleviation of symptoms patients are often unaware of the effects of the therapy and cannot provide reliable information regarding the efficacy of the therapy during the early stages of treatment. The current standards of psychiatric assessments may be inaccurate and incomplete. Recent research suggested that visual scanning parameters may provide objective markers that can support a more accurate assessment of neuropsychiatric disorders and better prediction of the efficacy of therapeutic approaches in patients.

Visual scanning devices and parameters derived from the analysis of visual scanning have been utilized when viewing images for a variety of purposes. For example, U.S. Pat. No. 7,857,452 relates to a method and apparatus for identifying the covert foci of attention of a person when viewing an image or series of images. The method includes the steps of presenting the person with an image having a plurality of visual elements, measuring eye movements of the subject with respect to those images, and based upon the measured eye movements triangulating and determining the level of covert attentional interest that the person has in the various visual elements.

United States Patent Application Publication No. US 2011/0270123 A1 relates to a method and apparatus of utilizing an eye detection apparatus in medical application, which includes calibrating the eye detection apparatus to a user; performing a predetermined set of visual and cognitive steps using the eye detection apparatus; determining a visual profile of a workflow of the user; creating a user-specific database to create an automated visual display protocol of the workflow; storing eye-tracking commands, for individual user navigation and computer interactions; storing context-specific medical application eye-tracking commands, in a database; performing the medical application using the eye-tracking commands; and storing eye-tracking data and result of an analysis of data from performance of the medical application, in the database. The method includes performing an analysis of the database for determining best practice guidelines based on clinical outcome measures.

Furthermore, U.S. Pat. No. 7,046,924 relates to a method for determining an area of importance in an archival image. In accordance with this method, eye information including eye gaze direction information captured during an image capture sequence for the archival image is obtained. An area of importance in the archival image is determined based upon the eye information. Area of importance data characterizing the area of importance is associated with the archival image.

Moreover, U.S. Re-issued Pat. No. RE39,539 E illustrates an apparatus for monitoring movement of a person's eye to monitor drowsiness.

Also, U.S. Pat. No. 7,206,022 relates to a camera system provided having an image capture system adapted to capture an image of a scene during an image capture sequence and an eye monitoring system adapted to determine eye information including a direction of the gaze of the eye of a user of the camera system. A controller is adapted to store the determined eye information including information characterizing eye gaze direction during the image capture sequence and to associate the stored eye information with the scene image.

United States Patent Application Publication No. US 2009/0012419 A1 discloses a system and method for performing physiological assessments.

United States Patent application Publication No. US 2008/0255949 A1 shows a method and system for measuring non-verbal and pre-conscious responses to external stimuli.

United States Patent Application Publication No. US 2007/0066916 A1 relates to a system and method for determining human emotion by analyzing eye properties.

U.S. Pat. No. 4,889,422 filed on Jan. 28, 1986 relates to a diagnostic device and method for detecting various neurological conditions, particularly dyslexia. Eye movement patterns of the subject to be tested are separated into saccadic movements (both progressive and regressive), vergence, pursuit movements and fixations, and the subject's specific eye movement pattern, as evaluated against a specific stimulus, and normal patterns is used for diagnostic purposes. A variety of eye movement detectors is disclosed, together with a sampling means which evaluates the eye position at intervals of less than 10 milliseconds.

United States Patent Application Publication No. US 20130090562 A1 relates to methods and systems for assessing cognitive function. The method includes the steps of presenting a plurality of images, wherein the plurality of images comprises a first subset of images and a second subset of images; monitoring eye movements of the subject during presentation of the first subset of images to obtain first eye movement data; monitoring eye movements of the subject during presentation of the second eye movement data; comparing the first eye movement data and the second eye movement data to determine an index of cognitive function; and correlating the index of cognitive function with a degree of cognitive function in the subject, thereby assessing the cognitive function. Wherein the monitoring steps are carried out using an optical eye tracking system.

SUMMARY OF THE INVENTION

It is an object of this invention to provide an improved method and system of identifying individuals with a neuropsychiatric disorder or to predict and determine the efficacy of treatment of the disorder.

It is an aspect of the invention to provide a method of identifying individuals with neuropsychiatric disorders or to predict and determine the efficacy of treatment of the disorder or detecting individuals who suffer a trauma to the brain by acquiring information about visual scanning behaviour and fluctuations of visual scanning behaviour of individuals comprising presenting to the individual a sequence of visual stimuli, wherein each visual stimulus is comprised of multiple images with specific characteristics, measuring the point-of-gaze of said subject on the visual stimuli and calculating a set of statistical measures that describes the visual scanning behaviour of the individual on images or portion of images with the same characteristics; and making a determination of biases in visual scanning behaviour of the individual, by comparing the statistical measures of the individual to the statistical measures of controls.

It is another aspect of the invention to provide a method of identifying the efficacy of a drug treatment for an individual with neuropsychiatric disorder comprising presenting to an individual undergoing treatment with said therapy a sequence of visual stimuli, wherein each visual stimulus is comprised of multiple images with specific characteristics, measuring the point-of-gaze of the individual on the visual stimuli and calculating a set of statistical measures that describes the visual scanning behaviour of the individual on images or portion of images with the same characteristics; and making a determination of changes to visual scanning behaviour of the individual by comparing to either the visual scanning behaviour when not undergoing treatment with said therapy or the visual scanning behaviour of the individual during said therapy; or the visual scanning behaviour of controls.

It is another aspect of the invention to provide a method of screening individuals for neuropsychiatric disorders comprising presenting to individuals sequences of visual stimuli, wherein each sequence is designed to identify a specific neuropsychiatric disorder or a specific symptom that is associated with a neuropsychiatric disorder; measuring the point-of-gaze of the individual on the visual stimuli and calculating a set of statistical measures that describes the visual scanning behaviour of the individual on image or portions of images with the same characteristics, for each of the sequences of visual stimuli; making determinations of biases in visual scanning behaviour of the individual for each of the different sequences of visual stimuli, by comparing the visual scanning behaviour parameters for each sequence with those of control groups; and combining the set of determinations of visual scanning behaviour biases to provide an objective quantitative measure of the patient's neuropsychiatric profile.

It is another aspect of the invention to provide a system for identifying an individual with a neuropsychiatric disorder or predict and determine the efficacy of treatment of a disorder comprising a visual scanning device to collect point-of-gaze data of individuals, compute parameters of visual scanning behaviour from the collected data, and compare the visual scanning behaviour parameters with those of controls.

It is yet another aspect of the invention to provide a system for identifying an individual with a neuropsychiatric disorder or determining the efficacy of treatment of a disorder comprising: an eye tracking system to monitor the visual scanning behaviour of individuals, and a computing device that includes a presentation module to configure to present visual stimuli on the monitor a data analysis module to compute statistical measures of the individual's visual scanning parameters from the eye trackers point-of gaze data, and to compare these measures with data from controls.

BRIEF DESCRIPTION OF THE FIGURES

FIGS. 3(a) and 3(b) is a chart representing that each fixation can be characterized by a set of parameters, and each fixation can be linked to a specific image or area of interest within an image.

FIG. 4 illustrates how the gaze position data is processed to create a sequence of fixations linked to images or areas of interest within images. In FIG. 4, visits are defined by all the fixations on a specific image or AOI that occur without moving away from the image or the AOI, respectively, to look at another image or AOI, respectively.

DETAILED DESCRIPTION OF THE INVENTION

Figure 1:
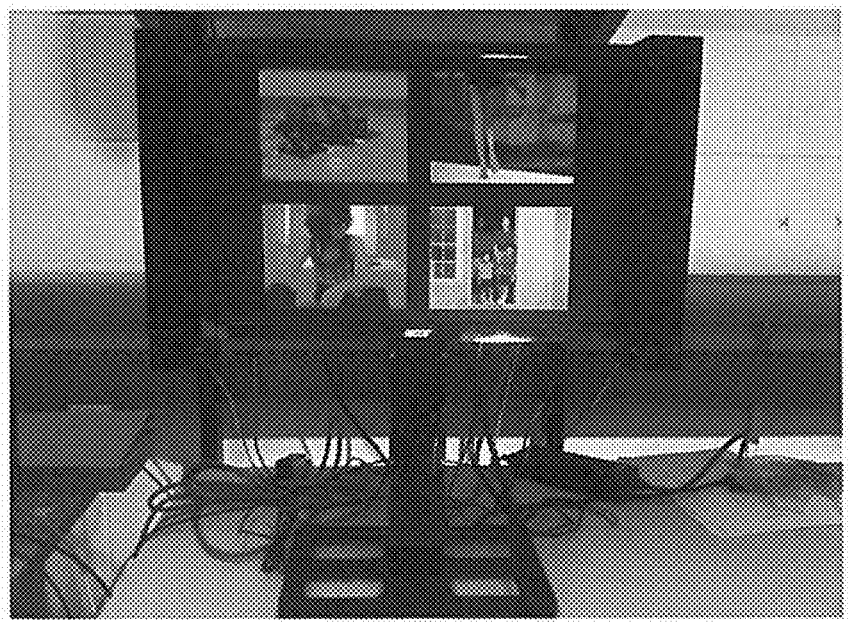
FIG. 1: Picture of an eye-tracking system and presentation monitor. The video camera of the eye-tracking system is in the monitor's stand and the infra red illuminators are in the two vertical opaque columns that are attached to the monitor.

In humans, detailed information (high resolution, colour, etc) of objects in the visual field (approximately 180°*135°) is obtained by moving the eyes so that images of these objects fall on the rod-free, capillary-free portion of the retina—the foveola—(0.3 mm, approximately 1°). During visual exploration, patterns of visual scanning are formed by successive periods of steady gaze (fixations) and rapid movements (saccades). Fixations allow areas in the subject's visual field to be viewed by the fovea, providing the visual system with high-acuity color-rich information, while less detailed information is collected by parafoveal and peripheral retinal fields. The patterns of movement (visual scanning behaviour) provide continuous records of regions in the visual field that are considered relevant by the subject.

Visual scanning behaviour (VSB) is controlled by both low-level perception processes (e.g., temporal and spatial characteristics of the visual stimuli) and high-level cognitive processes, which are driven by the subject's memories, emotions, expectations and goals. As such, VSB is affected by many of the processes that interact and contribute to the development and maintenance of neuropsychiatric disorders. VSB provides not only behavioural end products of cognitive processes but a continuous measure of attention (Hermans et al. 1999; Toh, Rossell, and Castle, 2011) that provides clues to the process through which these products are achieved. During natural viewing subjects are unaware of their eye movements and since VSB can be monitored without requests for meta-cognitive reports or other overt responses it provides information that generally can not be observed through the monitoring of patients' conscious behaviour.

The present invention uses parameters derived from the subject's VSB when viewing images to identify individual with neuropsychiatric disorders or to predict the efficacy of a treatment of a disorder. Examples of neuropsychiatric disorders and treatments that are provided in this document using the methods and systems of the present invention include, but not limited to, treatment of depression with antidepressant medication (SNRI), Identifying patients with Anorexia Nervosa and treatment of Anorexia Nervosa in a specialized intensive program at the hospital and identifying apathy in Alzheimer patients.

Methods of Assessing Neuropsychiatric Disorders

The method includes an eye tracking module configured to monitor the gaze position of the subject during viewing of visual stimuli, and a presentation module to present visual stimuli to the subject, wherein each visual stimulus is comprised of multiple images with specific characteristics. Since patients with neuropsychiatric disorders tend to selectively attend to disorder-relevant visual stimuli, often independently of awareness or intent (Mathews and McLeod, 1994), if the specific characteristics of the images are relevant to the disorder being probed, individuals with such a disorder will exhibit biases in their VSB when compared with individuals who do not suffer from the disorder. A computing module linked to the eye-tracking module to receive the gaze position data from the eye tracking module is utilized, to analyze the data and to derive a set of visual scanning parameters, and to compare the set of parameters for an individual with those of control subjects.

Figure 2:
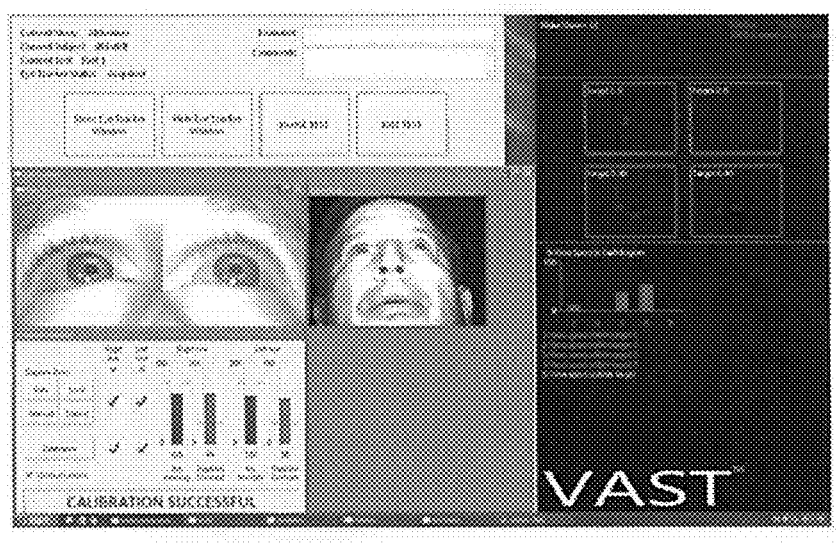
FIG. 2: Screen caption of the operator's monitor. Estimated gaze positions are shown in "real-time" in the upper-right hand corner of the screen. Total time spent on each of the four images on the current slide is presented in the bottom-right hand corner of the screen. The images from the eye-tracker's camera, metrics of eye-tracking quality, and eye-tracker controls are displayed in the bottom-left.

FIG. 1, shows an embodiment of such a system that was developed to carry out the neuropsychiatric assessment. The system (for example, Visual Attention Scanning Technology (VAST) developed by EL-MAR Inc. Toronto, Ontario, Canada) includes a gaze estimation system that records the participant's eye movements. However, other VSB systems can be used. The gaze estimation system (for example, EL-MAR Model VISION 2020RB) uses a digital video camera and multiple infra-red light sources to illuminate the patient's face. Images from the digital cameras are analyzed in real time by algorithms that were optimized to detect and estimates eye features [Guestrin and Eizenman, 2006, Guestrin and Eizenman, 2008]. The estimation of the point-of-gaze is derived from the estimation of the center of the pupil and corneal reflections (virtual images of light sources that illuminate the subject's face) in the images [Guestrin and Eizenman, 2006, Guestrin and Eizenman, 2008]. When a single camera is used, a calibration routine in which the subject is looking at several points (3-9) on the computer monitor has to be completed before the eye-tracker can be used to estimate gaze position accurately. When pairs of stereo-images are used a much simpler one-point calibration routine has to be completed before the eye tracking system can be used. The tracking range of the system described in this embodiment is ±30°, and it can accommodate head movements within a volume of 27000 $cm^3$. This allows participants to move their heads freely within 1 cubic foot, which supports natural viewing of the visual stimuli. Visual stimuli are presented on a computer monitor (for example, a 19 inch monitor) and each visual stimulus (slide) includes several distinct images. A second monitor is used by the VAST system (VAST is a trade mark of EL-MAR Inc.) to display the subject's fixation points on each image and provides the operator with an interface to control the experimental procedures (FIG. 2). Participants view a sequence of slides and the eye movement data is collected by a computer. The presentation, recording, and analysis of visual scanning parameters are controlled by computer programs in VAST.

The computer program product for assessing neuropsychiatric function comprises of code, which when loaded into memory and executed on a processor of a computing device, is designed to carry out a method to identify individual with neuropsychiatric disorders or to predict the efficacy of a treatment of a disorder comprising the steps of:
  a) Presenting images;
  b) Monitoring and recording eye movements during the presentation;
  c) Analyzing the data to obtain a set of parameters that characterizes the VSB;

d) Comparing the set of VSB parameters with those of controls.

The method of the present invention can use computing devices that include, but are not limited to, desk-top computers, portable computers, mobile computing devices such as tablets or cell phones with either internal eye-tracking devices (i.e., eye-tracking devices that are supported by the operating system of the computing devices) or eye-tracking devices that are external to the computing device (eg., data from the eye-tracker is transferred through one of the communication ports of the computing device).

The method of the present invention relies on the collection and analysis of the subject's visual scanning patterns when viewing visual stimuli. The collected gaze information is first divided to a set of discrete fixations. Fixations can be identified, for example, by clusters of gaze points that are within a specific distance (e.g. 1 degree) from each other for a time period that is greater than a minimum (eg., 200 milliseconds). Each fixation can be characterized by a set of parameters (FIG. 3(a)) such as: mean position on the display, duration and the order in the sequence of fixations from the time that a visual stimulus was presented. Each fixation is linked to a specific image on the display so that the fixation behaviour can be analysed with respect to the defining characteristics of images presented to the subject (see FIG. 3(b)) and with respect to the defining characteristics of specific regions (areas of interest) within an image. Some of these characteristics can be used to normalize the fixation behaviour (e.g., saliency).

The set of parameters defined in 3(a) is computed as follows: Fixation position is the average position of all the eye-position estimates that constitute the fixation. Fixation standard deviation is the standard deviation of all the eye-position estimates that constitute the fixation. Fixation start and fixation end are the time is milliseconds from the start of the experiment to the beginning and end of each fixation, respectively. The fixation order is the order of the fixation in the sequence that started with the first fixation on a new visual stimulus (eg. slide). The average pupil-size is the average of pupil-size estimates for data points that constitute the fixation.

If the average fixation position falls within the boundaries of an image or an area of interest (AOI) within an image, the characteristics of the image (e.g., valence, complexity) and the AOI within the image (e.g., color, corners) are recorded as part of the description of the fixation.

Figures 3, 4:
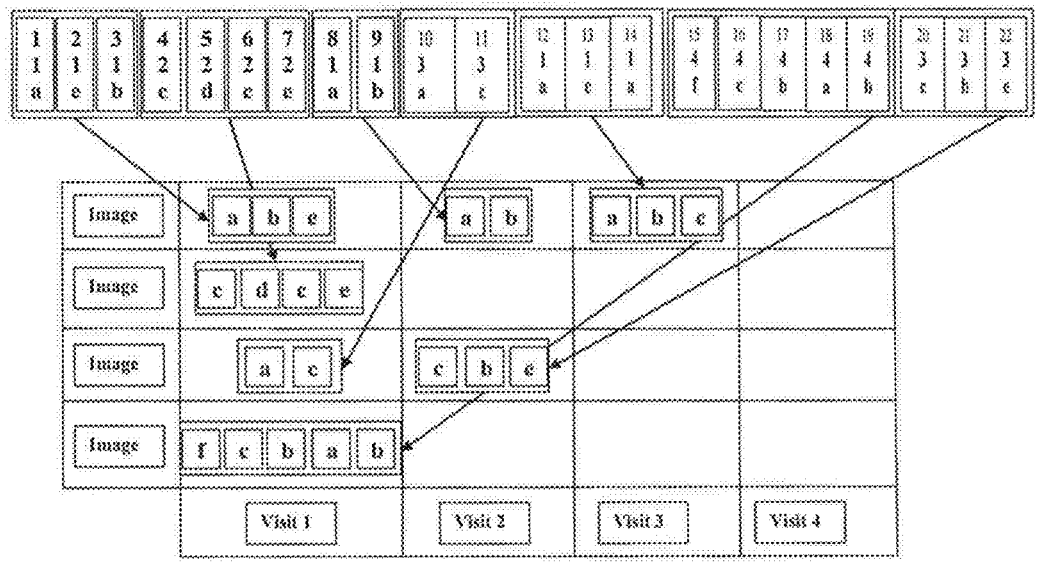
FIG. 4 is an example of gaze processing data.

Example of the processing of gaze position data is described in FIG. 4. The top row in FIG. 4 shows the order in which discrete fixations are detected. The second row from the top shows the images that are linked to each specific fixation and the third row from the top in FIG. 4 shows the area of interest in each image that is linked to each specific fixation. Using this procedure, visual scanning behaviour can be characterized both in terms of spatial fixation behaviour (i.e., fixations on specific areas of the visual stimulus), temporal fixation behaviour (i.e., fixations during sub-intervals of the scanning sequence) and event related fixation behaviour (i.e., fixations following a specific event). For example, as shown in FIG. 4, to determine the fixation behaviour during the second time that area of interest (a) of Image 1 was fixated on, one will look at the characteristics of the 8$^{th}$ fixation. As an example of an event related fixation behaviour one can characterise the fixation behaviour following a fixation on AOI (a) of Image 1. In the example of FIG. 4, the fixation following a fixation on AOI (a) of image 1 was always to AOI (b) of image 1.

FIG. 4: shows processing the gaze position data to create a sequence of fixations linked to images or areas of interest within images. Visits are defined by all the fixations on a specific image or AOI that occur without leaving the image or the AOI to look at another image or AOI.

A selection of visual scanning behavior parameters are defined as follows. This list is not intended to be limiting. These parameters pertain to VSB on whole images or areas of interest within images for the total presentation time of each stimulus or sub-intervals within the total presentation time (e.g., Image 3 Visit 1).

Figure 5:
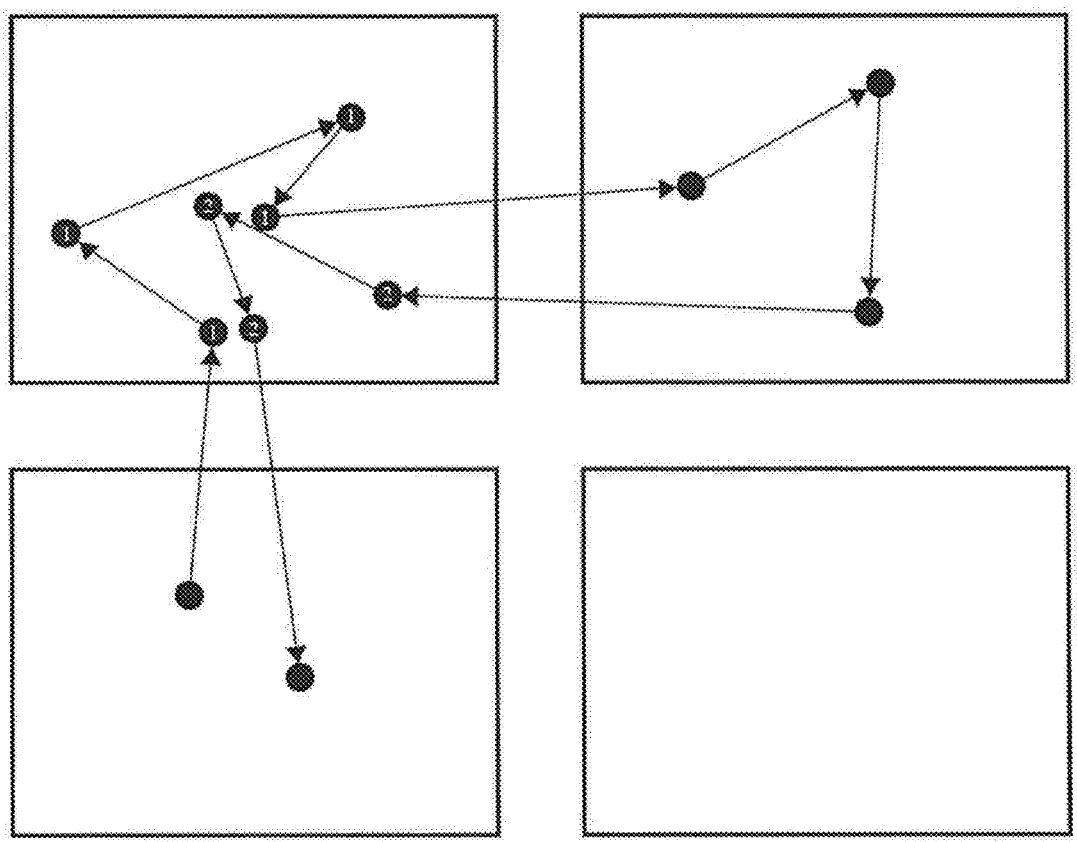
FIG. 5 is a diagram of a fixation sequence illustrating an example of data processing. The diagram depicts visits to the top-left image. Black dots represent fixations and arrows between dots represent saccades. Visit 1 and Visit 2 are marked for the top-left image.

Total number of fixations on each image or AOI within an image during each slide presentation.
Relative number of fixations: Total number of fixations on each image or AOI within an image divided by the total number of fixations on all images or AOIs on the slide.
Total duration of fixations on each image or AOIs within images during each slide presentation.
Relative duration of fixations: Total duration of fixations on each image or AOI within an image divided by the total number of fixations on all images or AOIs on the slide.
Total number of visits: A visit to an image or an AOI on an image starts with a fixation within the boundaries of this image or the AOI within the image and ends with a fixation outside the boundaries of this image or the AOI within the image (see FIG. 5). The total number of visits to an image or an AOI within an image is the number of visits during the whole slide presentation.
Relative number of visits: Total number of visit to each image or an AOI within an image divided by the number of visits to all images or AOIs on the slide.
Number of fixations within each visit.
Glance duration: The length of time of all fixations within each visit.
Glance duration before all images on the slide were seen.
Average glance duration: defined as the sum of all glance durations during each slide presentation divided by the number of visits.
Average glance duration before all images on the slide are seen.
Average glance duration after all images on the slide are seen.
Temporal fixation order.
Transition probabilities from an image or an AOI within an image to another image or another AOI.
Total scan path within an image or an AOI within an image. The sum of all horizontal and vertical eye movements within an image or an AOI within an image during the presentation of a slide.
Scan path within visit. The sum of all horizontal and vertical eye movements within an image or an AOI within an image during each visit.
Total dispersion of scan path: The variance of fixation positions within an image or an AOI within an image during the presentation of a slide.
Dispersion within a visit: The variance of fixation positions within an image or an AOI within an image during each visit.
Average dispersion per visit: The sum of all dispersions within visits divided by the number of visits.

Figure 6:
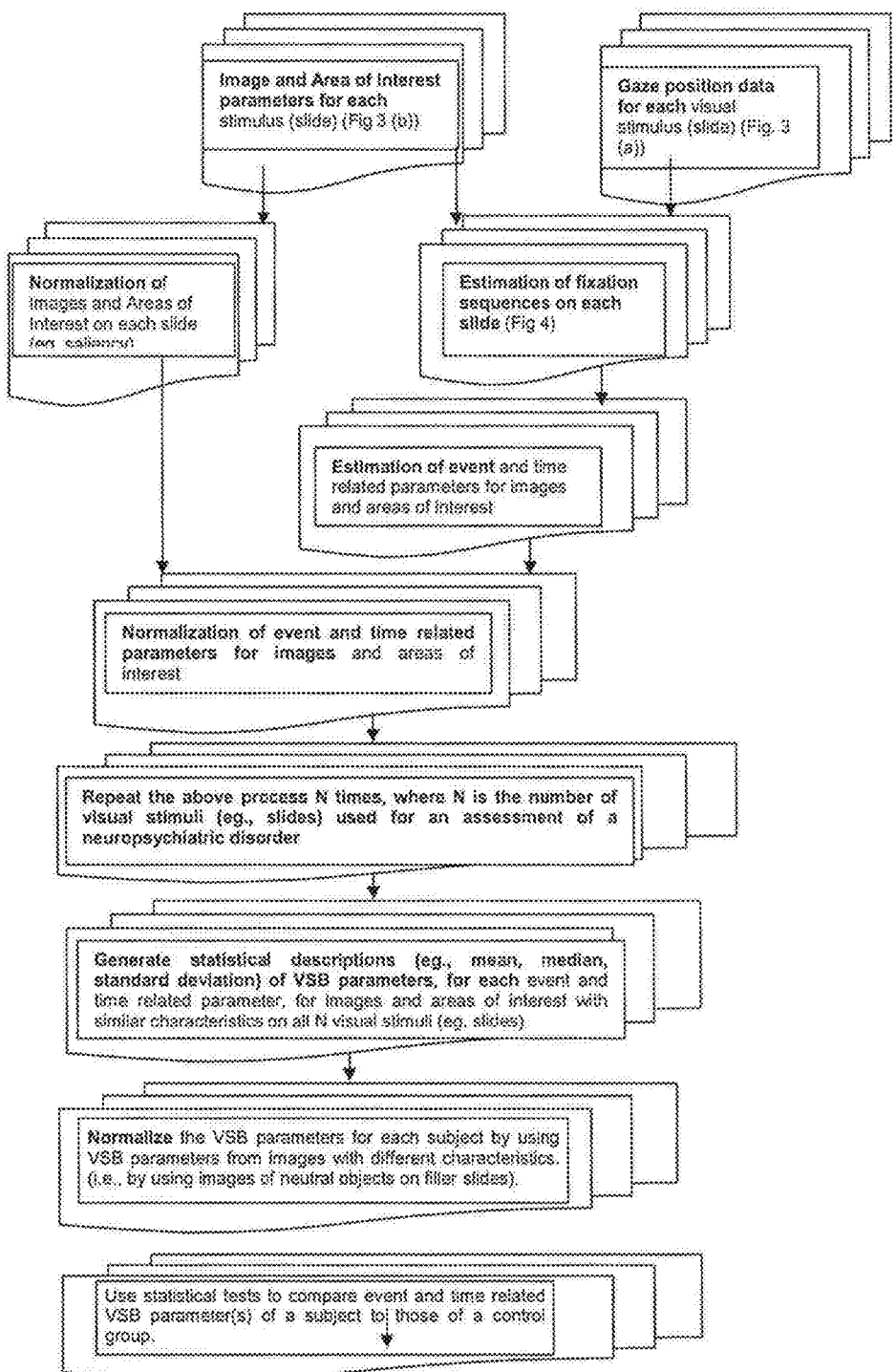
FIG. 6 is a general block diagram for data processing during the assessment task.

FIG. 6 provides a general block diagram for the processing sequence of a neuropsychiatric assessment. During the course of the assessment task, a series (N in FIG. 6) of visual stimuli (e.g., slides) is presented to the subject. The number of visual stimuli and the duration that each visual stimulus is determined by the assessment being conducted. For example, 50 slides are presented for 10.5 seconds each, for the assessment of the efficacy of treatment in depression while for the assessment of eating disorders 37 slides are presented for 12 seconds each.

In accordance with the present invention images on each slide are classified according to characteristics that include, for example, valance, arousal, dominance, complexity and thematic content (eg., sad, happy, angry, violence, suicide, neutral, thin, fat etc.).

In accordance with the present invention for each visual stimulus (eg. slide) gaze position data is processed to generate a set of VSB parameters for each image and/or AOI within an image, for the whole presentation interval or any sub-interval of the presentation and for all defined event related fixations. Following the processing of data from all visual stimuli (eg., slides), statistical descriptions (mean, median, Standard deviation) of VSB parameters for all images that share the same characteristics are computed. For each individual, the statistical description for one type of images (eg. sad, happy) can be normalized, for example, by subtracting the same statistical description for another type of images (eg., neutral). For example, if individuals tend to have short fixations or long fixation they will exhibit these patterns of fixations on both sad images and neutral images. By subtracting the VSB parameters of neutral images from that of sad images the manner in which individuals tend to scan an image, which might be independent of the content of the images, will be minimized.

In accordance with the present invention for each visual scanning parameter or a set of visual scanning parameters statistical tests that compare the statistical description(s) of the VSB of the individual being tested with the statistical description of the VSB of control groups to determine if the individual suffers from the specific disorder that the assessment task is designed to identify. The control group can be a group of individuals that do not suffer from the disorder that the assessment task is designed to identify or/and a control group of individuals that suffer from the disorder that the assessment task is designed to identify. In one embodiment of the assessment task, if the visual scanning parameter being tested falls outside the range defined by the mean of a control group ±rσ (where r is a constant to be decided for each assessment task and a is the standard deviation of the value of the parameter for control subjects) and inside the range defined by the mean±rσ of a control group of individuals that suffer from the disorder, the assessment task indicates that the individual suffers from the neuropsychiatric disorder that the assessment test is designed to identify.

In another embodiment of the present invention for each visual scanning parameter or a set of visual parameters, statistical tests compare the statistical descriptions of visual scanning parameters for the subject being tested before the start of treatment, for example, with the statistical description of the same subject during or after treatment for example.

The methods of the present invention can be carried out to assess many neuropsychiatric functions. Non-limiting examples of such assessments are set out below.

Identifying Individuals with Anorexia Nervosa and Determining the Efficacy of Treatment in Patients with Anorexia Nervosa Introduction Anorexia Nervosa (AN) is a severe and chronic neuropsychiatric disorder with one of the highest mortality rates of any psychiatric illness. AN is characterized by food restriction leading to weight loss, an extreme fear of fat or weight gain despite being underweight, body image distortion and a denial of the severity of the illness (American Psychiatric Association, 2000). Self-reported clinical assessment instruments, such as the Eating Attitudes Test (EAT-26) (Garner et. al., 1982), that are often used as screening tools are limited in utility when participants minimize or misrepresent their behaviour. It is estimated that only 30% of the population of people with AN actually receive treatment (Preti, et al., 2009) and the lack of objective indicators for anorexia nervosa impact identification, diagnosis and the course of treatment of the disorder (Pinhas and Bondy, 2010).

Traditional cognitive tests to measure attentional biases, such as the Stroop color naming interference test (Long et al, 1994) and the Dot-probe test (Shafran et al., 2007)) use reaction times to measure attentional biases. These indirect methods provide only a snapshot of the processes by which subjects allocate attention (i.e., attention is only measured at one specific instant of time). Therefore, these traditional methods suffer from low sensitivity and specificity. A more direct method to estimate attentional biases is to measure visual scanning behaviour (VSB), which provides continuous record of the attention allocation processes (Jansen et. al., 2005, George et. al., 2011, Giel et. al., 2011a, Wietersheim et al., 2012). Using visual scanning measures, George et al., (2011) showed that control subjects fixate mainly on the subject's abdominal region while patients with AN have wider fixation pattern that encompasses another body features such as hip and collar bones. Jansen et al, (2005) showed that participants who were extremely dissatisfied with their weight or shape focused on the ugly parts of themselves and the most attractive parts of others while participants who were satisfied with their bodies concentrated on the self-identified ugly parts of others. In a subsequent study of patients with AN, Wietersheim at al. (2012) showed that these attentional biases are often small and vary greatly. Even though group attentional biases in AN were identified in all of the above studies, the large variability between patients and the overlap between the visual scanning behaviour of patients and controls did not allow for robust detection (high sensitivity and specificity) of visual scanning biases in individual subjects with AN.

Using the methodology described in this invention we were able to show that patients with AN have visual scanning behaviour that is significantly different from that of control subjects. In the test that we developed to identify patients with AN, participants view visual stimuli (slides) with images of thin body shapes alongside images of social interactions for relatively long time-periods (12 seconds). Analysis of the measured visual scanning patterns showed that when visual scanning behaviour (VSB) of AN patients is compared to the VSB of control subjects, AN patients had significantly higher relative fixation times (RFTs) on images with thin body shapes and significantly lower RFTs on images with social interactions. The difference between the RFTs of AN patients and control subjects is maximized when the RFTs on social images are subtracted from the RFTs on images with thin or fat body shapes. We use the differences between the RFTs on thin body shapes and images with social interactions in individual subjects and a log-likelihood ratio (LLR) processor to detect biases in VSB of AN patients.

Participants

The patients in the participant behaviours all patients in a specialized eating disorder program. They all had confirmed/witnessed behaviours clinically that were consistent with AN and did not suffer from depression or OCD co-morbidity. The control group consisted of individuals who never had any known eating disorder or any other mental illness and who scored below the clinical cut point of 20 on the EAT-26 (Garner, et al., 1982).

A total of 20 patients with a diagnosis of AN and 23 controls participated in the study. Fourteen of the 20 AN patients were hospitalized at the time of the test while 6 had completed treatment and were in the process of recovery. The mean age of controls (14.4±1.82 years) was not significantly different from patients (AN: 15.00+1.73 years). The AN patients who were hospitalized at the time of the test (AN-pts) were analyzed subsequently separately from those that completed the treatment (AN-rec) as they no longer met full criteria for AN. The mean EAT-26 score for the AN-pts and control groups were 38.0±22.3 and 6.5±5.6 respectively (t(31)=6.07, P=$5.01 \times 10^{-7}$). Four of the AN-pt had a subclinical EAT-26 score (<20). These patients had either intentionally or unintentionally self-reported behaviour that was inconsistent with the other clinical data available and are considered unreliable historians (UH) for the purpose of the study. The proportion of UHs within the patient group (30.8%) is similar to the 27.6% found by Pryor, Johnson, Wiederman, and Boswell (1995) who described similar finding that they referred to as denial.

Visual Stimuli

Figure 7:
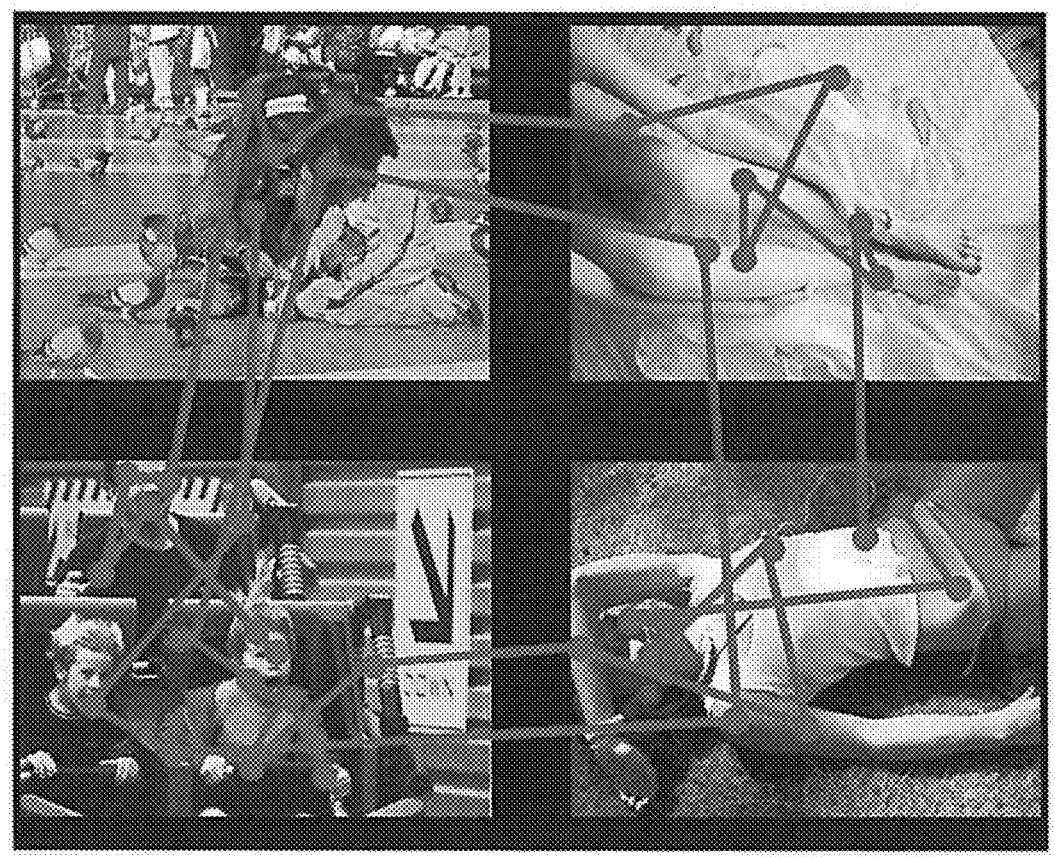
FIG. 7 is an illustration of a slide with images of thin body shapes (top right and bottom right) and social interactions (top left and bottom left). Gaze-position estimates are clustered spatially and temporally to obtain a sequence of fixations (circles) and saccades (lines between circles) that describe the visual scanning behaviour.

Visual stimuli were organized into slides that were presented on a computer monitor. Each slide had four images that were arranged in a 2×2 configuration (FIG. 7). Slides had two images of thin body shapes (e.g., visible rib cage or hipbone, full image of thin subjects) and two image of social interactions.

Subjects looked at 37 slides that included 16 test slides and 21 filter slides. Filler slides intended to mask the purpose of the experiment and had images that were neutral in content. The spatial position of images from each image type (e.g., thin body shapes, social interactions) were intermixed (i.e., for the set of 16 slides, each category of stimuli appeared in each quadrant of the slide the same number of times).

Methodology

The slides were presented on a 19" computer monitor that is part of EL-MAR's Visual Attention Scanning Technology (VAST, EL-MAR Inc. Toronto, Ontario, Canada). VAST incorporates a binocular gaze estimation system a real-time processor to estimate a set of visual scanning parameters (Elzenman et al., 2003, Hannula et al. 2010) and a monitoring station to supervise the procedure. Processing of eye-gaze data included the segmentation of gaze-position data to fixations, the association of fixations with images and the estimation of visual scanning parameters. The relative fixation time (RFT) on each image on each slide was calculated by dividing the total time of all fixations on the image by the total time of all fixations on all the images on the slide. The difference in relative fixation times (ΔRFT) on each slide was calculated by subtracting the average RFT on the social images on the slide from the average RFT on the images of thin body shapes on the slide. To detect VSB biases, the ΔRFTs for all test slides were processed by a log-likelihood ratio (LLR) processor. The processor first determines the likelihood that a measurement of a single ΔRFT is from an AN patient or from a control subject (Equation 1). Then, the processor calculates the log likelihood ratio for the set of measurements from each subject (equation 2). When the output of the LLR processor was greater than a threshold (log 1=0), the processor detected VSB biases that are consistent with the VSB of patients with AN.

In accordance with the present invention the LLR processor is one example of a statistical procedure to identify an individual with a neuropsychiatric disorder or to determine the efficacy of a treatment for the disorder.

The LLR Processor

To determine the likelihood that a measurement of a difference in the relative fixation time $\Delta RFT_j$ [ΔRFT] on slide j, is from a patient with AN is calculated by the likelihood ratio ($A_{T_j}$):

$$\Lambda_{T_j}(\Delta RFT_j) = \frac{P(\Delta RFT_j \mid \text{Class} = AN)}{P(\Delta RFT_j \mid \text{Class} = \text{Control})} j = 1 \ldots N \quad (1)$$

where, j=1 ... N are the test slides, $P(\Delta RFT_j|\text{Class}=AN)$ and $P(\Delta RFT_j|\text{Class}=\text{Control})(\Delta RFT_j|\text{Class}=\text{Control})$ are the conditional probability densities of $\Delta RFT_j$ for patients with AN and for controls, respectively. When $A_{T_j}$ is greater than 1, the measurement of $\Delta RFT_j$ more likely to come from a patient with AN than from a control subject. As visual scanning behaviour (VSB) is independent from slide to slide the log-likelihood ratio (LLR) processor for a set of N measurements is:

$$\log\left(\prod_{j=1}^{N} \Lambda_{T_j}\right) \quad (2)$$

When the output of the LLR processor is greater than a threshold (log 1=0), the processor detects VSB that is more consistent with that of a patients with AN than that or control subjects.

Figure 8:
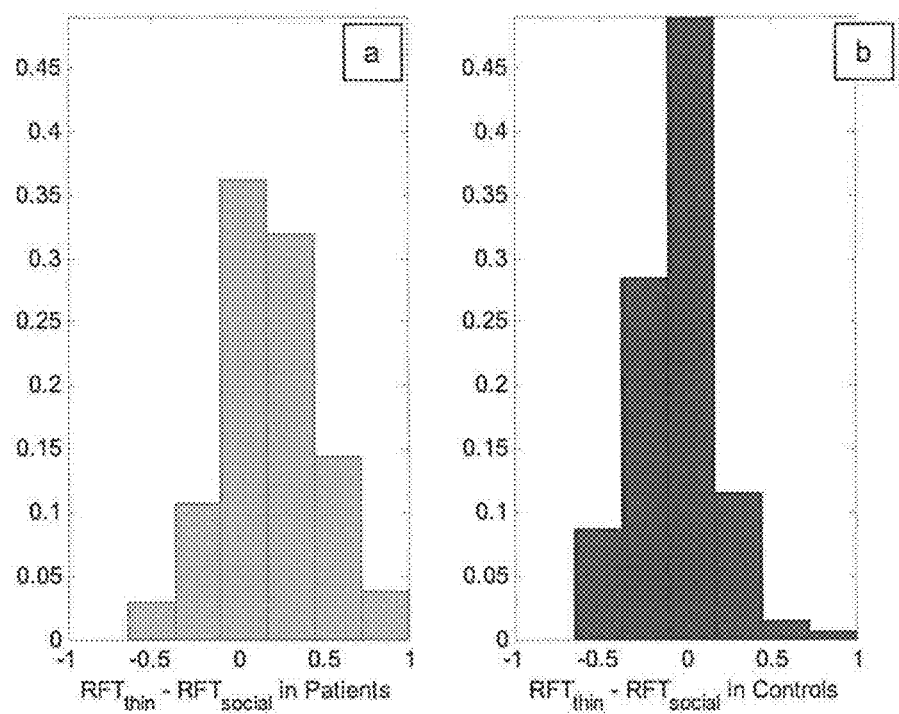
FIGS. 8a and 8b are histograms of the difference in relative fixation times on images with thin body shapes ($RFT_{thin}$) and images with social interaction ($RFT_{social}$) for patients with Anorexia Nervosa and controls, respectively. The boundaries of the bins were determined by dividing the range of the measured differences [−0.65 to 1] into 6 equal intervals.

FIG. 8 shows histograms of ΔRFT for patients with AN ($8_a$) and control subjects ($8_b$). (i.e., slides with thin body shapes and social interactions). The histograms in FIG. 8 were used in the calculations of the log-likelihood ratios (Equation 1 and 2). For each measurement, the conditional probability density was approximated by the height of the bin in the histogram that included that measurement. For each subject/patient the histogram were re-calculated from a data set that excluded the data for this patient/control, so that the calculations of the log-likelihood ratios for each patient/control were not biased by her own data (leave one out procedure).

Results

Figure 9:
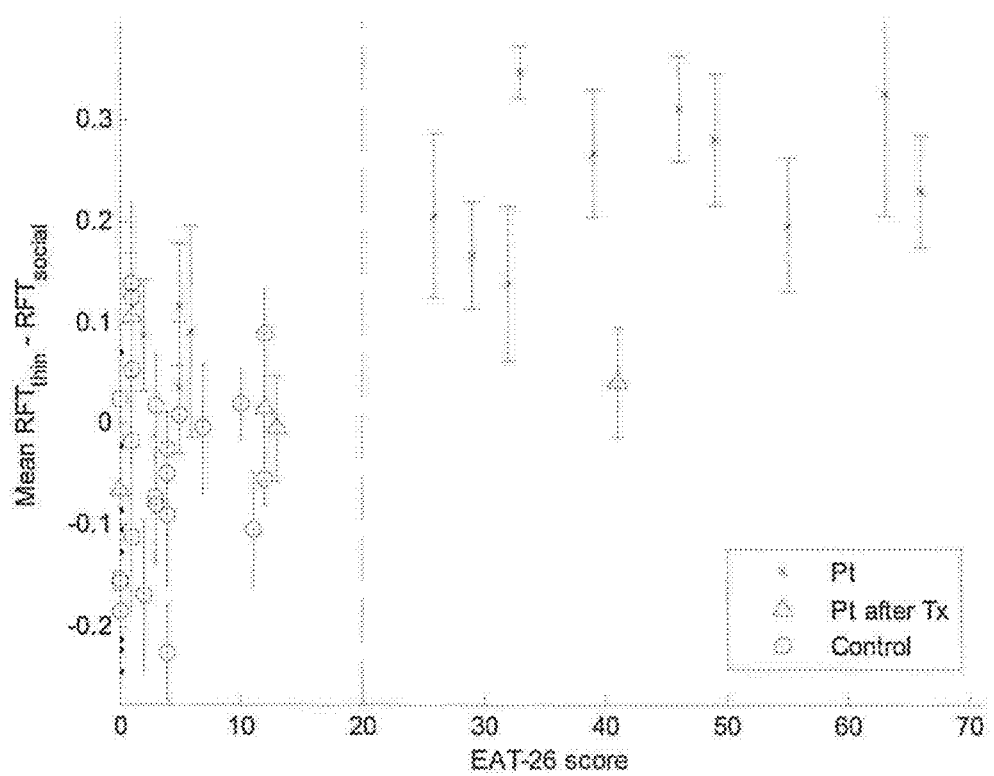
FIG. 9 shows the differences between the relative fixation times (RFTs) on images with thin body shapes and images with social interactions for individuals as a function of their EAT-26 scores. X's indicate the difference in mean RFTs of individual AN patients who were hospitalized when tested. Triangles indicate the difference in mean RFTs of individual AN patients that completed their treatment when tested. O's indicate the difference in mean RFTs of control participants (lines indicate ±1 S.D.).

FIG. 9 shows the differences between the RFTs on images with thin body shapes and the RFTs on images with social interactions ($\Delta RFT_{thin}$) for individual subjects, as a function of their EAT-26 scores. The dashed vertical line at an EAT-26 score of 20 indicates the clinical cut point. As a group, $\Delta RFT_{thin}$ for AN-pts (M=0.200, SD=0.098, range 0.036 to 0.348) is significantly larger (t(35)=7.335, P<0.001) than that of the control subjects (M=−0.044, SD=0.099, range −0.226 to 0.140). Also, as a group, the mean $\Delta RFT_{thin}$ of the six patients who completed their treatment (M=−0.006, SD=0.083, range −0.132 to 0.108) is not significantly different from the control group (t(27)=−0.878, P=0.388). The LLR processor detected biases in VSB that are consistent with the VSB of AN patients (i.e., the output of the processor is greater than 0) in 13/14 (sensitivity 93%) of the hospitalized patients and in 3 of the 23 control subjects (specificity 87%). Note that a very simple detector (e.g., $\Delta RFT_{thin}$>0) can be used to detect biases in VSB of AN-pts with relatively high sensitivity (100%) and specificity (65.3%). The LLR processor optimizes the performance of the detector when the optimization criteria is to maximize the sensitivity and specificity of the detector, simultaneously (i.e., the sum of sensitivity and specificity is maximized). VSB biases were detected in three of the four hospitalized patients that minimized their symptoms on the EAT-26 test and in one of the six AN-rec patients.

SUMMARY

The visual scanning behaviour of AN-pts who were hospitalized during the time of the tests is distinctly different from controls and patients that completed their treatment and are in the process of recovery. The relative fixation times (RFTs) on images with thin body shapes of these patients were higher than those of control subjects or patients that completed their treatment while their RFTs on images with social interactions were lower. Individual AN-pts with high RFTs on images with thin body shapes and low RFTs on social images had been ill and in treatment for over a year, were resistant to recovery clinically or were low weight at the time of the study. Clinically, patients that were most rigidly adherent to the cognitive patterns (preoccupation with thoughts about shape and weight, self-absorption and isolation from external influences) typical to AN had the largest biases in VSB. AN-pts with lower RFTs on images with thin body shapes and higher RFTs on images with social interactions began to normalize their eating patterns in treatment more readily. As these characteristics are not always predictable from the EAT-26 scores, the analysis of biases in VSB is useful in the prognosis and treatment of patients with AN.

Using a LLR-processor, biases in VSB that are consistent with the VSB of AN-pts were detected with high sensitivity (93%) when AN-pts looked at slides with images of thin body shapes and social interactions. Such biases were detected in only 13% of control subjects who looked at the same slides (high specificity—87%).

Biases in VSB that are consistent with the VSB of AN-pts were detected in three of the four AN-pts that either minimized or misrepresented their behaviour (patients with EAT-26 scores that are less than 20). The one patient for whom VSB biases could not be detected was a patient who was identified very early in her illness (duration of symptoms two months), had never had a severely low weight and clinically had relatively mild cognitive symptoms of weight and shape concerns. As biases in VSB are a reflection of attentional biases that tend to occur early in the information-processing sequence and are often independent of awareness or intent (Mathews & MacLeod, 1994) they often bypass the volitional component of self-report measures and are less available to conscious manipulation. As such, biases in VSB can provide a method to screen adolescents who may be minimizing or misrepresenting the presence of AN cognitions and behaviours.

In the six patients who completed an intensive treatment program (AN-rec), biases in VSB that were consistent with biases of AN-pts were detected in only one patient. This patient, whose score on the EAT-26 test was less than the clinical threshold, completed the treatment program only two days before she was tested after being ill for 5 years. AN-rec patients for whom no biases in VSB were detected completed the treatment program at least six months before they were tested. It is possible that the results for this patient demonstrate a transitional phase, where the fixed visual scanning pattern of AN-pts whose main focus is images with body/weight shapes is still present, but the patient is already aware of changes induced by the treatment program. One of the AN-rec patients for whom no biases in VSB were detected, had an EAT-26 score that was higher than the clinical cutoff (the EAT-26 score was 41). The lack of biases in VSB for this patient might also indicate a transitional phase, where the visual scanning pattern became more "normative" before the patients has become completely aware of all of the changes in her behaviour.

Observations

Using the methodology of this invention which enhances the differences between the visual scanning behavior of AN-pts and control subjects and a standard log-likelihood-ratio processor, biases in VSB of individual AN-pts can be detected with high sensitivity (93%) and specificity (87%). The inability to detect VSB biases in 83% of the patients who completed an intensive treatment program and were not hospitalized during the time of the study suggest that VSB biases are not traits of individual patients but rather reflect the state of patients during the time of the test (i.e., the biases can be used to monitor the progress of treatment). Biases in VSB were detected in three of the four AN-pts that either minimized or misrepresented their behaviour (patients with EAT-26 scores that are less than 20). Since biases in VSB often bypass the volitional component of self-report measures and are less available to conscious manipulation they might help to identify subjects who are at risk of developing anorexia nervosa. Such an objective physiological indicator is important since a significant proportion of the adolescent AN population is unable or unwilling to self identify.

Since patients with eating disorders are preoccupied with the ability to control their eating habits, using the methodology of this invention with images of low or high calorie food, for example, can be used to identify biases in visual scanning behaviour that are associated with this pre occupation. For example, visual stimuli can include images of positive eating habits (low calorie food eaten in controlled circumstances) and negative eating habits (high calorie foods being eaten in an uncontrolled fashion, e.g., binge like with fingers) to differentiate patients with Anorexia Nervosa (AN) from patients with Bulimia Nervosa. While both groups of patients tend to avoid food images (when compared to controls), BN patients tolerate images of negative eating habits better than patients with AN and therefore have longer fixation times on such images (as compared to patients with AN). Using images of low and high calorie food provide another objective marker to identify patients with eating disorders (i.e., a marker that is different from that obtained by using body shapes) and can be used to differentiate between different groups of patients with eating disorder (eg., AN and BN).

By using the method of this invention with different sets of disorder-relevant visual stimuli (single or multiple slide presentations), biases in visual scanning behaviour to visual stimuli (images) that probe different characteristics of the same disorder (eg., for eating disorders—body shapes and low and high calorie food) or different neuropsychiatric disorders can be obtained. For example, if the Image set that is used to detect apathy (later in this document) is used with the image set that is used to identify AN patients, the extent to which patients with AN also suffer from apathy can be quantified. By using several sets of images, where each set probes a different neuropsychiatric disorder (e.g., depression, apathy, etc.), biases in visual scanning behaviour that are associated with each neuropsychiatric disorder can be obtained. The set of biases in visual scanning behaviour can then provide an objective measure of the patient's psychiatric profile (i.e., a model of the patient's psychiatric state).

Determining the Efficacy of Drug Treatment in Patients with Major Depression Disorder Introduction Depression is a syndrome that tends to be chronically recurring and affects about 20% of the population worldwide. Antidepressant medication, which increases the levels of certain brain neurotransmitters (e.g., norepinephrine or serotonin) that are lacking in depressed people, is the most common treatment for depression. The most popular class of antidepressant medication is SSRI's (selective serotonin reuptake inhibitors—Prozac, Zoloft, Paxil, Luvox) but there are several major classes of antidepressant drugs (SNRIs—effexor, Serzone; Bupropion—Wellbutrin; Mirtazapine—Remeron; TCAs (Tricyclics)—Elavil, Pamelor, Norpamin; and MAOIs (MAO inhibitors)—Parnate, Nardil). One of the more enduring and problematic problems in treating depression is associated with the fact that only 50% of patients respond to a specific drug and that the actual therapeutic effect of significant alleviation of depressive symptoms may not appear until after 2-6 weeks of daily dosing. The existence of this time lag and the inability to predict if drug treatment will be effective for specific patients pose significant clinical problems. If the treatment turns out not to be effective, precious treatment time has been lost, translating into increased risk for serious consequences and increased suffering for the patient. A method to predict whether a treatment was destined to be efficacious and therefore should be continued, or if not, should be abandoned in favour of a different drug or drug class would be of great value. The method of this invention describes such a method.

Using analysis of natural visual scanning behaviour (i.e., patients look naturally at images on a computer monitor), Eizenman et. al. (2003), and later Kellough et al. (2008) found that when compared with controls, depressed subjects have longer fixation times on dysphoric images and had difficulty shifting attention away from these images. Based on these initial observations the methods of this invention were developed to predict the efficacy of treatment in individuals with major depression disorder.

Participants

Thirty four patients with Major Depressive Disorder participated in the study. All patients were evaluated by a psychiatrist and met the DSM-IV-TR criteria for Major Depression. Following a baseline visit (Visit 2), patients received 60 mg Duloxetine antidepressant monotherapy (SNRI) PO once daily for the duration of the study.

TABLE 1

Study Flowchart.

| VISIT | V1 (Screen)* | V2 | V3 | V4 | V5 | V6 | V7 | V8 |
|---|---|---|---|---|---|---|---|---|
| Week | −1 | 0 | 1 | 2 | 3 | 4 | 5 | 6 |
| Informed Consent | X | | | | | | | |
| Medical & Psychiatric Hx | X | | | | | | | |
| Demographics | X | | | | | | | |
| Entry Criteria | X | | | | | | | |
| Physical Exam | X | | | | | | | |
| Vitals (Wt, Ht) | X | | | | | | | |
| Urine Drug Screen | X | | | | | | | |
| MINI | X | | | | | | | |
| Blood pressure, pulse | | X | | X | | X | | X |
| HDRS-17 | | X | X | X | X | X | X | X |
| Visual Scanning | | X | X | X | X | X | X | X |
| Adverse Events | | X | X | X | X | X | X | X |
| Medication Compliance | | X | X | X | X | X | X | X |
| Review of Concurrent Medication | X | | X | X | X | X | X | X |

Prior to the start of the drug medication treatment, the visual scanning patterns of each patient were measured a(V2 visit) Then, each patient had their visual scanning patterns recorded once per week for a further six weeks.

Visual Scanning Task

Figure 10:
FIG. 10 is an example of a test slide for the prediction of drug efficacy in depression. The slide has two dysphoric (low valence) images (top and bottom left) and two social (high valence) images (top and bottom right).

Subjects' visual scanning patterns were recorded as they view a presentation of visual stimuli. The visual stimuli were organized as a series of slides with four images per slide. Images were selected from libraries such as the International Affective Picture System (IAPS) [Lang et al., (1999)] and photos.com. Each image was classified with respect to its thematic content (e.g, social interaction, homelessness), complexity (simple to complex, 1-10) and was rated for valence and arousal. Valence is a measure of a subject's relative pleasure in viewing an image, while arousal classifies subject reaction to an image in the continuum from relaxed to excited. Valence, arousal, thematic content and complexity were the criteria used to select images on each slide. The four images for the early detection of drug efficacy in depression included two dysphoric images and two images with social interactions. The positions of the images on the slide were assigned randomly. Dysphoric images displayed themes of loss and sadness, illness and despair while images with social interactions presented themes of interpersonal attachment and social content. Dysphoric images were selected to have valence ratings below 4 (low valence), while images with social interactions were rated above 6 (high valence). Images on the same slide have similar arousals and complexities. An example of a test slide is shown in FIG. 10.

Each slide presentation included also filler slides that have images with similar characteristics (themes, valence, arousal, complexity) and are used in the analysis to normalize the scanning patterns of individual subjects. The slide presentation used 15 test slides with dysphoric and social themes and 20 filler slides. The positions of the four images on each test slide were randomly changed between sessions. Each slide was presented for 10.5 seconds for a total presentation time of 8 minutes and 45 seconds. Participants sat at a distance of approximately 65 centimeters from the monitor so that the visual angle subtended by each of the four images on each slide is approximately (15.2°×11.4°). The horizontal and vertical separation between any two images is greater than 2.5°.

To predict the efficacy of drug treatment we used the following VSB parameters: 1) the average number of visits to dysphoric images prior to the start of the medication treatment 2) the average number of fixations during visit 1 prior to the start of the medication treatment, and 3) the direction of change in relative fixation time on dysphoric images during the first week of medication.

Results

Figure 11:
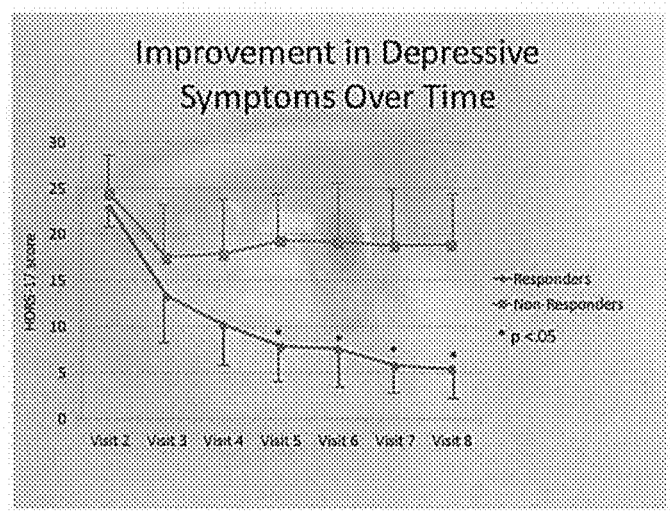
FIG. 11 HAMD scores for patients who responded to the medication (responders) and for patients who did not respond to the medication treatment (non-responders). The scores are provided for the full length of the study (8 weeks).

After 8 weeks, a psychiatrist classified 17 of the 34 patients who participated in the study as responders to the medication (had a HDRS-17 of half their initial value in their last visit) and 17 patients as non-responders. FIG. 11 shows the HDRS-17 scores for the two groups FIG. 11: Means and standard deviations of HDRS-17 scores for responders (blue) and non-responders (red) for the 34 patients who participated in the study. After 8 weeks, 17 patients were classified as responders and 17 patients were classified as non-responders. Asterisks indicate significant differences at a level of α=0.05.

Figure 12:
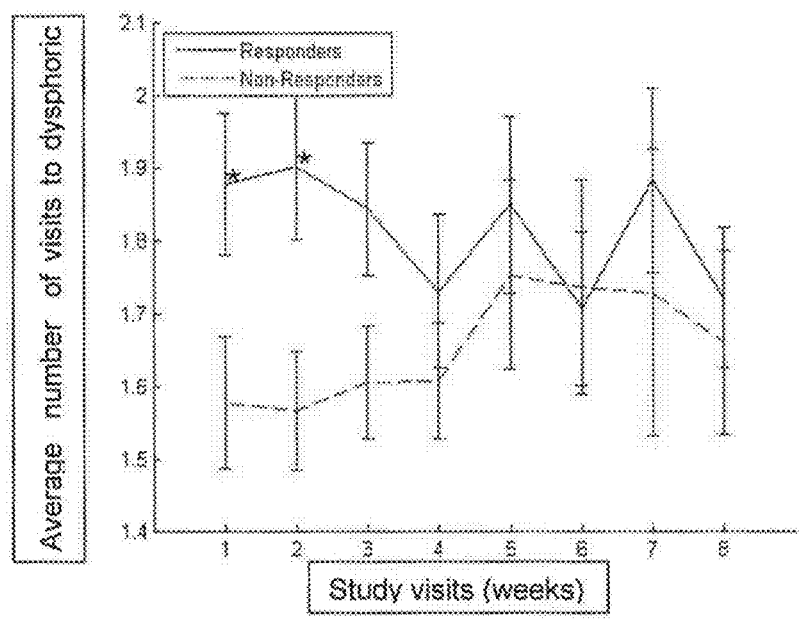
FIG. 12 shows the means and standard deviations (lines indicate ±1 S.D.) of the number of visits to dysphoric images for the 8 weeks of the study for responders (solid line) and non-responders (dashed line).
Figure 13:
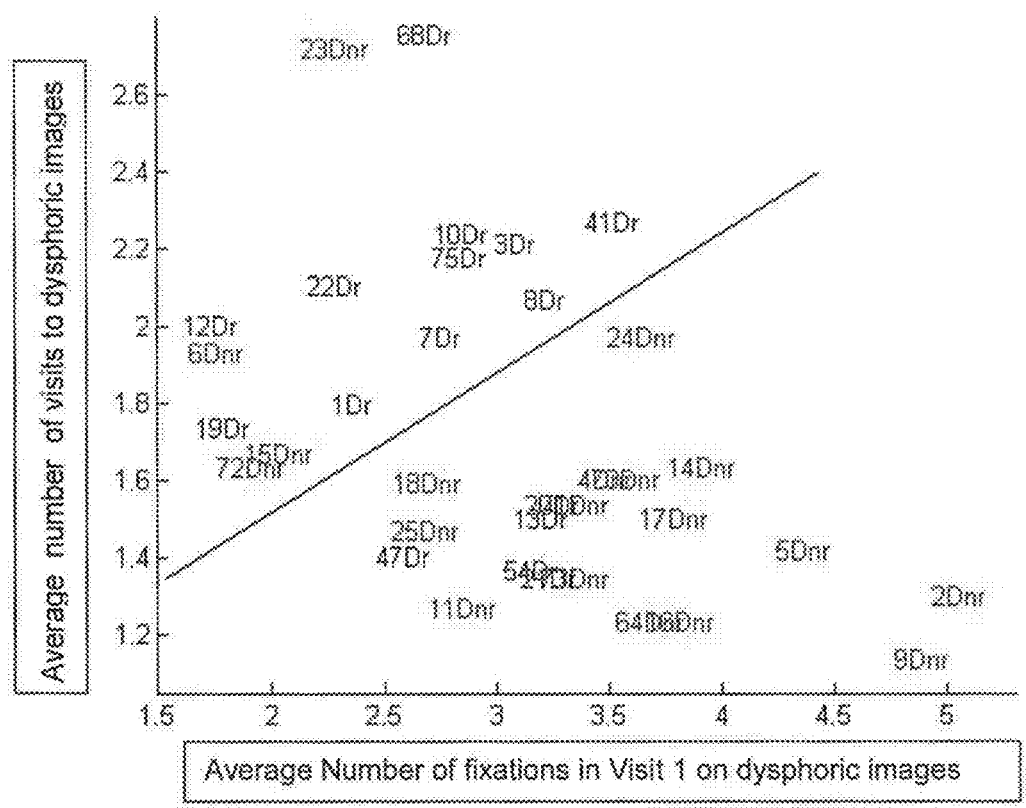
FIG. 13 shows the average number of visits to dysphoric images versus the average number of fixations during the first visit to dysphoric images by individual patients with major depression disorder. The data for each patient includes a reference number (eg, 9) and a designation Dr or Dnr. Dr (Depressed responders) are patients that responded to the drug treatment and Dnr (Depressed non-responders) are patients that did not respond to the drug treatment. For each patient the (x,y) coordinates of the center of the D correspond to the mean values of the number of fixations in Visit 1 (x-coordinate) and the average number of visits to dysphoric images (y-coordinate). The classifier is illustrated by a simple line. Patients with VSB parameters that are above the line are classified as responders and patients with VSB parameters below the line are classified as non-responders.

FIG. 12 shows that as a group prior to the start of medication (i.e, before Visit 3) there are significant differences (α=0.05) in the number of visits to dysphoric images between responders and non responders. As a group, the number of visits to dysphoric images of responders in Week 2 (M=1.91, SD=0.94) is significantly higher (α=0.013) than the number of visits to dysphoric images of non responders (M=1.57, SD=0.83).

As a group, the number of fixations during the first visit of responders in Week 2 (M=2.56, SD=0.13) is significantly lower (α=0.03) than the number of fixations during the first visit of non-responders (M=3.15. SD=0.209). Using the above two VSB parameters, and a linear line (see FIG. 12) that defines the boundary of a classifier for responders and non-responders (patients with VSB parameters that are above the line are classified as responders) the test can predict the response to drug treatment with a sensitivity of 64.7% and a specificity of 76.5%, prior to the start of treatment. The classifier has a positive predictive value (PPV) of 73.3% and a negative predictive value of 68.4%.

When the direction of changes in the relative fixation times on dysphoric images during the first week of treatment (i.e., if the relative fixation time on dysphoric images is lower in the third visit than the relative fixation time in the second visit), is used by the classifier, the specificity of classifier is increased to 86.4% and the sensitivity to 58.3% with a PPV of 70% and NPV of 79.2%. These results show that after one week of treatment the detector/classifier can predict who will not respond to the drug treatment with high accuracy (86.4%).

Identifying Apathy in Alzheimer Patients

Introduction

In patients with Alzheimer disease (AD) it is important to differentiate between apathetic and non-apathetic patients as the diagnosis of apathy affects the course of treatment. Assessing Alzheimer patients is a difficult and imprecise task that requires highly trained personnel. An objective method to identify apathy in Alzheimer patients will have significant clinical implications for diagnosis and pharmacological treatment. The current invention provides an objective method to identify patients with apathy.

Participants 31 patients (ages 77.2±9.2 years) with AD were tested. 15 of the AD patients had apathy (NPI-apathy>4 (Robert et al., 2009) and 16 were non-apathetic Alzheimer patients. Additionally 21 Age matched non-AD participants (ages 71.4±8.4 years) were tested as a control group. AD patients were screened for apathy using the Neuropsychiatric Inventory (NPI) apathy subscale. The Modified Mini Screen (MMS) was administered to healthy controls to exclude those with marked neuropsychiatric disturbances. As a group the mean NPI-apathy for the non-apathetic AD patients was 0.8±1.1 and for the AD patients with apathy, 5.9±2.6.

Methodology

Participants were tested with the VAST system (EL-Mar Inc. Toronto, Ontario). The study slides included 16 test slides and 10 filler slides. The slides were presented sequentially, with each slide presented for 10.5-seconds. The total duration of the assessment was less than 5 minutes. Each test slide included four images: two images of neutral objects (low arousal and moderate valence), one image of social interactions (high valence and high arousal) and one dysphoric image (low valence and high arousal). Images were selected from the standardized International Affective Picture System (IAPS) (Lang et. al, 1999) and from photos.com. AD patients with apathy scan images with different characteristics in a similar manner so that differences in VSB parameters when images with large differences in valence and/or arousal are viewed, are smaller than the differences observed when non-apathetic AD patients and age matched controls view the same images. In this example of the current invention, the difference in relative fixation times on images with social interactions and neutral images is used to identify AD patients with apathy.

Results

Figure 14:
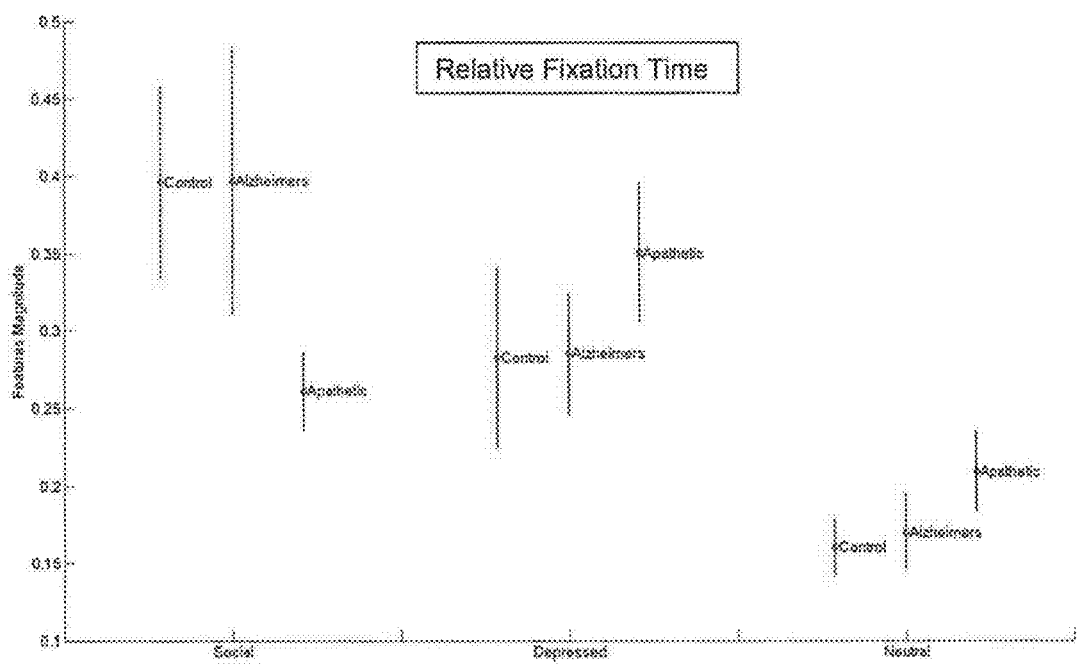
FIG. 14 illustrates the relative fixation times of apathetic Alzheimer patients, Alzheimer patients and age matched controls on social, dysphoric and neutral images.

FIG. 14, shows the relative fixation times of the three groups of participants (AD, AD-apathetic and age-matched controls) on three different types of images (social, dysphoric and neutral). Age matched controls and non-apathetic AD patients have similar relative fixation times on all three types of images. Apathetic AD patients show significantly different visual scanning patterns. Alzheimer patients with apathy have significantly lower relative fixation times on images with social interactions when compared with AD patients who are not apathetic (α=0.04) and age matched controls (α=0.01) and significantly higher relative fixation times on neutral images when compared with age matched controls (α=0.02).

When differences between the relative fixation times on social images and neutral images are used for the identification of apathy (using a naive Baysian Classifier), 67% of the AD patients with apathy were identified as apathetic, 72% of the non-apathetic AD patients were classified as non-apathetic and 78% of the control subjects were classified as non apathetic.

Other

The foregoing embodiments of the invention are examples and can be varied in many ways. Moreover, the invention includes detecting individuals who suffer a trauma to the brain (for example a concussion, whether from sports or otherwise) and might develop symptoms similar to those observed in individuals with neuropsychiatric disorders. Such variations or modifications are intended within the scope of the following claims.

REFERENCES

1) American Psychiatric Association (2000). *Diagnostic and statistical manual of mental disorders: Fourth Edition. Text Revision* (DSM-IV). Washington, D.C.: American Psychiatric Association.
2) Bauser, D. A. S., Suchan, B., Duan I., (2011). Differences between perception of human faces and body shapes: Evidence from the composite illusion. *Vision Research*, 51:195-202.
3) Dobson, K. S., Dozois, D. J., (2004). Attentional biases in eating disorders: a meta-analytic review of Stroop performance. *Clinical Psychology Review*, 23(8):1001-1022.
4) Downing, P. E., Jiamg, Y., m Shuman, M., Kanwisher, N., (2001). A cortical area selective for visual processing of the human body. *Science*, 293:2470-2473.
5) Eizenman, M., Yu, L. H., Grupp. L., Eizenman, E., Ellenbogen, M., Gemar M., Levitan, R. D. (2003). A naturalistic visual scanning approach to assess selective attention in major depressive disorder. *Psychiatry Research*, 118(2): 117-128.
6) Fairbum C. G., Cooper Z., Shafran R. (2003). Cognitive Behaviour therapy for eating disorders: a "transdiagnostic" theory and treatment. *Behaviour Research and Therapy*, 41, 509-528.

7) Garner. D. M., Olmsted, M. P., Bohr, Y., Garfinkel, P. E. (1982). The eating attitudes test: psychometric features and clinical correlates. *Psychological Medicine,* 12(4): 871-8.

8) Garner, D. M., Vitousek, K. M., Pike, K. M. (1997). Cognitive-behavioral therapy for anorexia nervosa. In D. M. Garner & P. E. Garfinkel (Eds.), *Handbook of treatment for eating disorders* (pp. 94-144). New York: Guilford Press.

9) Garner, M. Mogg, K., & Bradley, B. P. (2006). Orienting and maintenance of gaze to facial expressions in social anxiety. *J Abnorm Psychol,* 115(4), 760-770.

10) George H. R., Cornelissen P. J., Hancock P. J. B., Vivinlemi V. V., and Tovee M. J., (2011). Differences in eye-movement patterns between anorexic and control observers when judging body size and attractiveness. *British Journal of Psychology,* 102, 340-354.

11) Giel, K. H., Friederich, H. C., Teufel, M., Hautzinger, M., Enck, P. and Zipfel, S., (2011a). Attentional processing of food pictures in Individuals with Anorexia Nervosa—An Eye-Tracking study. *Biological Psychiatry* 69, 661-667.

12) Giel, K. H., Teufel, M., Friederich, H. C., Hautzinger, M., Enck, P. and Zipfel. S., (2011b). Processing of pictorial food stimuli in patients with eating disorders—a systematic review. *International Journal of Eating Disorders* 44:2 105-117.

13) Guestrln, E. D., Eizenman, M., (2006). General theory of remote gaze estimation using the pupil center and corneal reflections. IEEE Transactions on Biomedical Engineering 53(6):1124-33.

14) E. D. Guestrin and M. Eizenman, "Remote point-of-gaze estimation for studies of selective attention and mood disorders", Presented at the $30^{th}$ Canadian Med. Biol. Conf. (CMBEC30), Toronto, ON, Canada, June 2007.

15) E. D. Guestrin and Eizenman M. Remote point-of-gaze estimation requiring a single-point calibration for applications with infants. Proceedings of ETRA 2008, pages 267-274, March 2008.

16) Hannula, D. E., Althoff, R. R., Warren, D. E., Riggs, L., Cohen N. J., and Ryan J. D., (2010). Worth a glance: using eye movements to Investigate the cognitive neuroscience of memory. *Frontiers in human Neuroscience,* 4: Article 166, 1-13.

17) Hermans, D., Vansteenwegen, D., Eelen, P., (1999). Eye Movement Registration as a Continuous Index of Attention Deployment: Data from a Group of Spider Anxious Students. *Cognition & Emotion.* 13(4):419-34.

18) Jansen. A., Nederkoom, C., Mulkens, S., (2005). Selective visual attention for ugly and beautiful body parts in eating disorders. *Behavior Research and Therapy,* 43(2): 183-96.

19) Johansson, L., Ghaderi, A., Andersson, G., (2005). Stroop interference for food- and body-related words; a meta-analysis. *Eating Behaviors* 6(3):271-281.

20) Kellough, J. L., Beevers, C. G., Ellis, A. J. Wells, T. T., "Time course of selective attention in clinically depressed young adults: An eye tracking study," Behaviour Research and Therapy, Vol. 46, No. 11, Pp. 1238-1243, 2008.

21) Lang, P. J., Bradley, M. M., Cuthbert, B. N., 1999. International Affective Picture System: Instruction Manual and Affective Ratings. Technical Report A-4, University of Florida—The Center for Research in Psychphysiology, Gainsville, Fla.

22) Long, C. G., Hinton, C., Gillespie, N. K., (1994). Selective processing of food and body size words: application of the Stroop Test with obese restrained eaters, anorexics, and normals. *International Journal of Eating Disorders.* 15(3):279-83.

23) McKhann G, Drachman D, Folstein M, et al. (1984), Clinical diagnosis of Alzheimer's disease: report of the NINCDS-ADRDA Work Group under the auspices of Department of Health and Human Services Task Force on Alzheimer's Disease. Neurology. 34 (7): 939-44.

24) Mathews. A., and MacLeod. C., (1994). Cognitive approaches to emotion and emotional disorders. *Annual Review of Psychology,* 45, 25-50.

25) Pinhas, L., & Bondy, S. J. (2010). Epidemiology of eating disorders in Children and Adolescents. In J. Lock (Ed.), *The Oxford Handbook of Child and Adolescent Eating Disorders: Developmental Perspectives* (Vol. 1). New York: Oxford University Press.

26) Preti, A., Girolamo, G., Vilagut, G., Alonso, J., Graaf, R. Bruffaerts, R., et al. (2009). The epidemiology of eating disorders in six European countries: results of the ESEMeD-WMH project. *Journal of Psychiatric Research,* 43(14), 1125-1132.

27) Rinck, M., Becker E. S., (2006). Spider fearful individuals attend to threat, then quickly avoid it: evidence from eye movements. *Journal of Abnormal Psychology* 115(2):231-8.

28) Robert P, Onyike C U, Leentjens A F, et al. (2009), Proposed diagnostic criteria for apathy in Alzheimer's disease and other neuropsychiatric disorders. Eur Psychiatry. March; 24 (2): 98-104.

29) Sears, C. R., Thomas C. L., Lehuquet J. M. Johnson C. S., (2010). Attentional biases in dysphoria: An eye-tracking study of the allocation and disengagement of attention. *Cognition and emotion,* 24(8), 1349-1368.

30) Shafran R., Cooper Z., and Fairbum C. G., (2002). Clinical perfectionism: a cognitive-behavioural analysis. *Behaviour Research and Therapy,* 40, 773-791.

31) Shafran, R., Lee, M., Cooper, Z., Palmer, R. L., Fairbum, C. G., (2007). Attentional bias in eating disorders. *International Journal of Eating Disorders,* 40(4):369-80.

32) Shafran, R., Lee, M., Cooper, Z., Palmer, R. L., Fairbum, C. G., (2008). Effect of Psychological Treatment on Attentional Bias in Eating Disorders. *International Journal of Eating Disorders,* 41(4):348-354.

33) Smeets, E', Tiggemann, M., Kemps, E., Mills J. S., Hollitt, S., Roefs, A., Jansen, A., (2011). Body Checking Induces an Attentional Bias for Body-Related Cues. *International Journal of Eating Disorders,* 44:50-57.

34) Toh, W L, Rossell S L., Castle D J, 2011, Current visual scabpath research: a review of investigations into the psychotic, anxiety, and mood disorders, Comprehensive Psychiatry, Vol. 52 PP. 567-579.

35) Wietersheim J., Kunzi, F., Hoffmann, H., Glaub, J., Rattler E., Rraue C., (2012). Selective Attention of patients with Anorexia Nervosa While looking at pictures of their own body and bodies of others: An Exploratory Study. *Psychosomatic Medicine,* 74:107-113.

We claim:

1. A method of identifying an individual with a neuropsychiatric disorder or determining the efficacy of treatment of the neuropsychiatric disorder or detecting an individual who suffers a trauma to the brain and might develop symptoms similar to those observed in said individual with the neuropsychiatric disorder, whereby said method of identifying, determining or detecting are performed by acquiring information about visual scanning behaviour and fluctuations in visual scanning behaviour of said individual with said neuropsychiatric disorder, and said individual who suffers a trauma to the brain comprising:
(a) presenting to the individual with said neuropsychiatric disorder or trauma a sequence of visual stimuli, wherein each visual stimulus is presented at a random position in the sequence and is comprised of competing images with characteristics, that are selected according to said neuropsychiatric disorder or trauma, where said competing images have different scores on scales that quantify said selected characteristics, and are presented simultaneously to the individual with said neuropsychiatric disorder or trauma; and wherein said visual stimuli do not influence said neuropsychiatric disorder or trauma:
(b) measuring the point-of-gaze of said individual on the visual stimuli and calculating statistical measures that describes the visual scanning behaviour of the individual on images or portions of images with the selected characteristics;
(c) making a determination of biases in the visual scanning behaviour of the individual, by comparing the statistical measures of the individual in step (b) to the statistical measures of controls; and
(d) wherein the statistical measures that describe the visual scanning behaviour of the individual in step (b) are normalized by subtracting the contributions of at least one parameter that is different from the selected characteristics and affect the statistical measures that describe the visual scanning behaviour of that individual.

2. The method of claim 1 wherein said disorder is major depression disorder, eating disorder, anxiety disorder, bipolar disorder, obsessive-compulsive disorder, schizophrenia, drug addiction, attention deficit disorder, attention deficit hyperactivity disorder, Alzheimer's disease, apathy, dementia, a learning disorder, or post traumatic syndromes.

3. The method of claim 1 wherein said method is a method of determining the efficacy of treatment of the disorder, where treatment of the disorder includes drug treatment, cognitive behaviour therapy and specialized treatment programs offered by psychiatrists or hospitals for neurological disorders.

4. The method of claim 1 wherein said method is a method of detecting an individual who suffers trauma to the brain and might develop symptoms similar to those observed in said individual with the neuropsychiatric disorder, wherein said trauma includes mild traumatic brain injury, traumatic brain injury or stroke.

5. The method of claim 1 wherein said method is a method of detecting an individual who suffers trauma to the brain and might develop symptoms similar to those observed in said individual with the neuropsychiatric disorder, wherein said symptoms include depression, apathy, lack of empathy, impatience or a combination thereof.

6. The method of claim 1, wherein the selected characteristics comprise subject matter, colour, symmetry, complexity, valence, arousal, dominance, or a combination thereof.

7. The method of claim 1, wherein the statistical measures of visual scanning behaviour include mean, median and variance of spatial, temporal and event related parameters of eye fixations.

8. The method of claim 7 where parameters of eye fixations include the number of fixations, relative number of fixations, duration of fixations, relative duration of fixations, spatial distribution of fixations, temporal distribution of fixations, number of visits, relative number of visits, number of fixations within visit, glance duration, glance duration before a fixation event, glance duration after a fixation event, temporal fixation order, transition probabilities from/to an image or an area-of-interest, scan path, scan path within visit, scan path dispersion, or scan path dispersion within visit.

9. The method of claim 7 where the parameters of said eye fixations include an ordered sequence of image characteristics that are linked to fixations, an ordered sequence of the duration of fixations or an ordered sequence of positions of fixations or a combination thereof.

10. The method of claim 7 where a parameter that is different from the selected characteristics include an image characteristic that was not selected or an eye fixation parameter that is affected by the individual's general visual scanning strategies and is independent of the content of the images.

11. The method of claim 1, wherein the determination of biases comprises the comparison of normalized statistical measures of the individual visual scanning behaviour with those of controls using confidence intervals, likelihood ratio detectors, linear classifiers, non-linear classifiers, neural networks that are trained with the parameters of eye fixations or a combination thereof.

12. The method of claim 1, wherein controls are individuals not diagnosed with said disorder.

13. The method of claim 1, wherein controls are individuals diagnosed with said disorder.

14. The method of claim 1 wherein said competing images are discrete with non-overlapping boundaries.

15. The method of claim 1 wherein said visual stimuli are presented on a display of a desk-top computer, portable computer, a mobile device, a tablet or a cell phone.

16. The method of claim 1 wherein contributions of a parameter that is different from the selected characteristics and affect the statistical measures that describe the visual scanning behaviour of an individual are measured on images with characteristics that are different from the selected characteristics.

17. A method of identifying the efficacy of a treatment for an individual with a neuropsychiatric disorder or trauma comprising:
(a) presenting an individual undergoing the treatment with a sequence of visual stimuli, wherein each visual stimulus is presented at a random position in the sequence and is comprised of competing images with characteristics that are selected according to said neuropsychiatric disorder or trauma, where said competing images have different scores on scales that quantify the said selected characteristics, and are presented simultaneously to the individual undergoing the treatment, and wherein said visual stimuli do not influence said neuropsychiatric disorder;
(b) measuring the point-of-gaze of the individual on the visual stimuli and calculating statistical measures that describes the visual scanning behaviour of the individual on the competing images or portions of the competing images with the selected characteristics; and
(c) making a determination of changes in visual scanning behaviour of the individual by comparing the statistical measures in step (b) to one of the statistical measures of the individual when not undergoing treatment with said therapy, the visual scanning behaviour of the individual during said therapy, and the visual scanning behaviour of controls; and
(d) wherein the statistical measures that describe the visual scanning behaviour of the individual in step (b)

are normalized by subtracting the contributions of at least one parameter that is different from the selected characteristics and affect the statistical measures that describe the visual scanning behaviour of that individual.

18. A method of screening individuals for neuropsychiatric disorders or trauma comprising:
(a) presenting to an individual sequences of visual stimuli, wherein each sequence of visual stimuli is designed to identify a specific neuropsychiatric disorder or a specific symptom that is associated with a neuropsychiatric disorder, wherein each visual stimulus is presented at a random position in the sequences and is comprised of competing images with characteristics that are selected according to the said neuropsychiatric disorders or symptoms, where said competing images have different scores on scales that quantify the said selected characteristics, and are presented simultaneously to the individual; and wherein the visual stimuli do not influence said neuropsychiatric disorders or trauma;
(b) measuring the point-of-gaze of the individual on the visual stimuli and calculating a set of statistical measures that describes the visual scanning behaviour of the individual on competing images or portions of competing images with selected characteristics, for each of the sequences;
(c) making a determination of biases in the visual scanning behaviour of the individual for the different sequences of visual stimuli, by comparing the statistical measures for each sequence of visual stimuli with the statistical measures of a group of individuals who suffer from the same neuropsychiatric disorder or trauma that said sequence of visual stimuli is designed to identify;
(d) using the determination of biases in visual scanning behaviour to provide an objective quantitative measure of the individual's neuropsychiatric profile or trauma; and
(e) wherein the statistical measures that describe the visual scanning behaviour of the individual, for each sequence from said sequences in step (b), are normalized by subtracting the contributions of at least one parameter that is different from the selected characteristics for each sequence from said sequences and affect the statistical measures that describe the visual scanning behaviour of that individual.

* * * * *